(12) United States Patent
DeVincenzo et al.

(10) Patent No.: US 7,281,923 B1
(45) Date of Patent: Oct. 16, 2007

(54) ORTHODONTIC ANCHOR APPLIANCE

(76) Inventors: John DeVincenzo, 1312 Garden St., San Luis Obispo, CA (US) 93401; Craig Jacobson, 1611A S. Melrose Dr., PMB16, Vista, CA (US) 92081; Steven O. Luse, 1611A S. Melrose Dr., PMB16, Vista, CA (US) 92081

( * ) Notice: Subject to any disclaimer, the term of this patent is extended or adjusted under 35 U.S.C. 154(b) by 0 days.

(21) Appl. No.: 11/414,431

(22) Filed: May 1, 2006

(51) Int. Cl.
*A61C 3/00* (2006.01)

(52) U.S. Cl. .......................... 433/18; 433/173

(58) Field of Classification Search ............ 433/17–24, 433/173, 174, 176; 623/17.17–19; 606/61, 606/70
See application file for complete search history.

(56) References Cited

U.S. PATENT DOCUMENTS

| | | | |
|---|---|---|---|
| 5,853,291 A * | 12/1998 | DeVincenzo et al. | 433/176 |
| 6,827,574 B2 * | 12/2004 | Payton | 433/8 |
| 6,896,514 B2 * | 5/2005 | DeVincenzo | 433/24 |
| 2003/0104335 A1 * | 6/2003 | Chung | 433/18 |
| 2004/0147931 A1 * | 7/2004 | De Clerck | 606/70 |
| 2004/0166461 A1 * | 8/2004 | Devincenzo | 433/18 |
| 2005/0142513 A1 * | 6/2005 | Hotta | 433/18 |
| 2005/0147938 A1 * | 7/2005 | Devincenzo et al. | 433/18 |
| 2006/0069389 A1 * | 3/2006 | Knopfle | 606/61 |

\* cited by examiner

*Primary Examiner*—Cris Rodriguez
*Assistant Examiner*—Sunil K. Singh
(74) *Attorney, Agent, or Firm*—Rodgers & Rodgers

(57) ABSTRACT

An orthodontic anchor appliance having elongated titanium anchor plate adapted for attachment to bone, anchoring tab formed on the emerging end of the anchor plate, a nontitanium sleeve enveloping the anchoring tab, and an elongated bar attached to the sleeve.

7 Claims, 1 Drawing Sheet

ORTHODONTIC ANCHOR APPLIANCE

BACKGROUND OF THE INVENTION

Skeletal anchors have been used in maxillo-facial surgery for a number of years in the form of semiflexible titanium anchors with multiple screw holes. The screws are attached to various bone components so that the bones can be attached together either because of accidental fractures or man-made surgical adjustments. These types of anchors are now being used in orthodontics with modifications so that forces are applied to objects other than teeth such that the equal and opposite reactions of Newtonian physics is avoided. In orthodontics, these anchors are termed skeletal anchors and attach to cortical bone beneath the apices of the teeth. Often, two or three such anchors are placed in a particular arch for movement of selected teeth.

At times, the skeletal anchor is not able to be positioned in an ideal location or a need arises for the point of force application to be at some distance from the emergence of the skeletal anchor. The skeletal anchors are always made of titanium while any attachment is always made of a stainless steel alloy. The advantage of stainless steel is that soldering and welding can occur with ease which is not possible with titanium. This allows for the attachment of orthodontic fixtures to extend force applications to teeth positioned remote from the anchor.

BRIEF SUMMARY OF THE INVENTION

An orthodontic anchor appliance having an elongated anchor plate with multiple apertures formed therein for attachment to bone by means of screws and the like, an anchoring tab formed on the emerging end of the anchor plate and having an aperture formed therein, an elliptical slot formed in the anchor between the anchor plate and anchoring tab, a pair of shoulders formed on the periphery of the anchor in general alignment with the elliptical slot, a sleeve positioned over the anchoring tab, and an elongated bar attached to the sleeve.

DETAILED DESCRIPTION OF THE INVENTION

Figure 1:
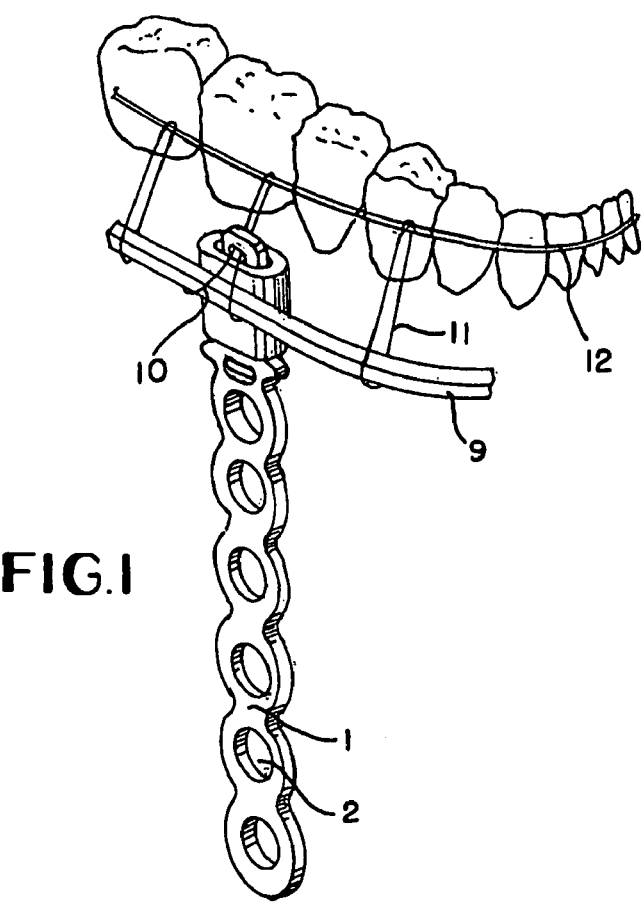
FIG. 1 is a perspective view of the orthodontic anchor appliance according to this invention.

In the drawings and with particular reference to FIG. 1, the numeral 1 designates the anchor plate having multiple apertures 2 formed therein. In an orthodontic application, anchor plate 1 is placed adjacent the teeth and secured to cortical bone by means of screws inserted through apertures 2, as is well known.

Figure 2:
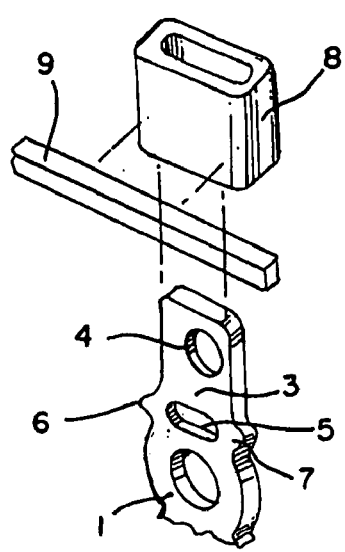
FIG. 2 is an exploded partial perspective view of the appliance.

As best shown in FIG. 2, anchoring tab 3 is integrally joined to the emerging end of anchor plate 1 with elliptical slot 5 disposed therebetween. Also, shoulders 6 and 7 are formed at the outer periphery of the junction between the emerging end of anchor plate 1 and anchoring tab 3 at the opposite ends of elliptical slot 5 and in general alignment therewith. In order to adapt anchor plate 1, which is made of titanium, for use in orthodontics, means are necessary to direct force vectors at various distances to selected teeth. In order to accomplish this result, sleeve 8 is made of stainless steel or other like material and is adapted to engage anchoring tab 3. In practice, hollow sleeve 8 is placed over anchoring tab 3 whereby the lower edge of sleeve 8 comes into abutting contact with shoulders 6 and 7 thereby preventing further downward movement of sleeve 8.

Since sleeve 8 is made of stainless steel, elongated bar 9 is attachable thereto by soldering, welding and the like. In order to ensure that sleeve 8 is secured in position, wire 10 can be looped around elongated bar 9 and through aperture 4, formed in anchoring tab 3, and tightened by means of an appropriate knot. Alternatively, a short section of wire can be placed through aperture 4 and twisted so as to prevent disengagement of sleeve 8.

With elongated bar 9 in place, elastomeric bands 11 are placed anywhere along elongated bar 9 and then extended to the desired location on archwire 12, which is attached to the patient's teeth by means of brackets, as is well known.

Figure 3:
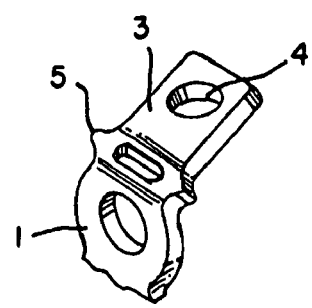
FIGS. 3 and 4 are enlarged perspective views showing details of the anchoring tab.
Figure 4:
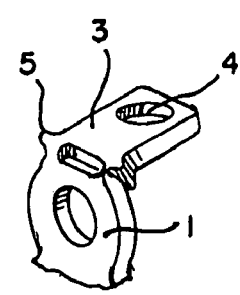

At times it is desirable to reorient the position of elongated bar 9 with respect to anchoring plate 1. In FIGS. 3 and 4, anchoring tabs 3 are shown to be bendable at an angle of 45° in FIG. 3 and 90° in FIG. 4 with respect to anchoring plate 1. The bending of anchoring tab 3 is facilitated by elliptical slot 5 due to the reduced amount of metal material at the junction of the bend.

Therefore, by this invention, an orthodontic anchoring appliance is provided using a titanium anchor plate such that tension can be applied to a patient's teeth and, at the same time, eliminating the necessity to apply tension from one tooth to another.

The invention claimed is:

1. An orthodontic anchor comprising in combination an elongated anchor plate, at least one aperture formed in said anchor plate, said anchor plate having an emerging end, an anchoring tab integral with said emerging end at a junction, a hollow sleeve enveloping said anchoring tab, said sleeve having an upper end, said anchoring tab extending beyond said upper end, an aperture formed in said portion of said anchoring tab extending beyond said sleeve, an elongated bar welded to said sleeve so that said elongated bar remains in contact with said sleeve, a wire enveloping said elongated bar and extending through said aperture formed in said anchoring tab, and said elongated anchor plate being titanium and said sleeve being stainless steel.

2. An orthodontic anchor according to claim 1 wherein a pair of shoulders are disposed at the outer periphery of said junction.

3. An orthodontic anchor according to claim 2 wherein a slot is disposed between said emerging end and said anchoring tab.

4. An orthodontic anchor according to claim 2 wherein said sleeve comprises a lower edge, and said lower edge is in abutment with said shoulders.

5. An orthodontic anchor according to claim 3 wherein said slot is elliptical and said anchoring tab is bendable about said elliptical slot.

6. An orthodontic anchor according to claim 3 wherein aid pair of shoulders are in general alignment with said slot.

7. An orthodontic anchor comprising in combination an elongated anchor plate, at least one aperture formed in said anchor plate, and said anchor plate having an emerging end, an anchoring tab integral with said emerging end at a junction, a hollow sleeve enveloping said anchoring tab, said sleeve having an upper end, said anchoring tab extending beyond said upper end, an aperture formed in said portion of said anchoring tab and extending beyond said sleeve, and a short wire extending through said aperture with the ends thereof being twisted.

* * * * *